(12) United States Patent
Schinazi et al.

(10) Patent No.: US 7,325,572 B2
(45) Date of Patent: Feb. 5, 2008

(54) FLOW RESTRICTOR DEVICE FOR A MEDICAL APPARATUS

(76) Inventors: Robert G. Schinazi, 320 Pomelo Dr., Apt. #193, Vista, CA (US) 92081; Lauren E. de Rosset, 320 Pomelo Dr., Apt. #193, Vista, CA (US) 92081

( * ) Notice: Subject to any disclaimer, the term of this patent is extended or adjusted under 35 U.S.C. 154(b) by 31 days.

(21) Appl. No.: 11/299,313

(22) Filed: Dec. 9, 2005

(65) Prior Publication Data

US 2007/0131296 A1    Jun. 14, 2007

(51) Int. Cl.
*F16L 55/027* (2006.01)

(52) U.S. Cl. .............. 138/43; 138/42; 138/46; 604/247; 604/252

(58) Field of Classification Search ........... 138/43, 138/42, 46; 604/247, 252
See application file for complete search history.

(56) References Cited

U.S. PATENT DOCUMENTS

| | | | | |
|---|---|---|---|---|
| 1,964,300 A | * | 6/1934 | Perry et al. | ............... 138/43 |
| 2,021,079 A | * | 11/1935 | Mittendorf et al. | .......... 138/42 |
| 2,236,084 A | * | 3/1941 | Brown | ................. 138/43 |
| 2,341,394 A | * | 2/1944 | Sloan | ................. 251/120 |
| 2,511,733 A | * | 6/1950 | Morrison | ................. 138/43 |
| 2,857,927 A | * | 10/1958 | Pardee | ................. 137/549 |
| 3,552,444 A | * | 1/1971 | Levesque | ................. 138/43 |
| 3,815,636 A | * | 6/1974 | Menzel | ................. 239/542 |
| 3,998,427 A | * | 12/1976 | Bentley | ................. 251/208 |
| 4,022,384 A | | 5/1977 | Hoyle et al. | |
| 4,150,696 A | * | 4/1979 | Meier et al. | ............... 138/44 |
| 4,200,119 A | | 4/1980 | Cunningham | |
| 4,411,292 A | | 10/1983 | Schiller | |
| 4,589,872 A | | 5/1986 | Bellin et al. | |
| 4,738,665 A | * | 4/1988 | Shepard | ............... 604/248 |
| 4,796,660 A | | 1/1989 | Bron | |
| 5,032,264 A | | 7/1991 | Geiger | |
| 5,156,680 A | | 10/1992 | Orzechowski | |
| 5,609,303 A | | 3/1997 | Cohen | |
| 5,779,361 A | * | 7/1998 | Sugiura | ............... 366/340 |
| 6,497,685 B1 | | 12/2002 | Dennehey et al. | |
| 6,550,956 B1 | | 4/2003 | Utracki et al. | |
| 6,569,128 B1 | | 5/2003 | Christensen et al. | |
| 6,981,967 B2 | | 1/2006 | Massengale et al. | |

OTHER PUBLICATIONS

Co-pending U.S. Appl. No. 10/791,682, filed Mar. 2, 2004.
Co-pending U.S. Appl. No. 10/909,752, filed Aug. 2, 2004.

* cited by examiner

*Primary Examiner*—James Hook
(74) *Attorney, Agent, or Firm*—Dority & Manning (57) ABSTRACT

A medical apparatus flow restrictor includes a housing having an inlet and an outlet, and a fluid flow path defined through the housing between the inlet and outlet. At least one pair of opposed restriction surfaces are provided in contact with each other within the housing between the inlet and the outlet. The restriction surfaces are disposed in the flow path such that fluid delivered to the inlet passes between the opposed restriction surfaces prior to flowing from the outlet. At least one of the restriction surfaces comprises a pattern of fluid passages formed into the surface, the passages having a size and shape and cooperating with the opposed restriction surface such that a desired flow rate of fluid is achieved through the restrictor.

23 Claims, 11 Drawing Sheets

FLOW RESTRICTOR DEVICE FOR A MEDICAL APPARATUS

RELATED APPLICATION

The present application is related by subject matter to pending U.S. application Ser. No. 10/791,682 filed on Mar. 2, 2004, and U.S. application Ser. No. 10/909,752 filed on Aug. 2, 2004.

FIELD OF THE INVENTION

The present invention relates generally to the field of flow restriction devices, and more specifically to a flow restrictor that is particularly well suited for regulating the flow of fluids in various medical devices and systems.

BACKGROUND OF THE INVENTION

There are various applications of flow restriction devices in the medical arts for closely regulating the flow of a fluid. One common use of such devices is with an infusion pump system wherein fluid medicine or other fluids are delivered to an injection site on the patient from an infusion pump. Embodiments are known wherein the flow restrictor is contained within the pump body. For example, U.S. Pat. No. 4,386,929 describes a short capillary tube contained within the pump housing for regulating the flow of dispensed medication. It is also known to include a flow restrictor downstream of the infusion pump, for example as with the delivery tube system described in U.S. Pat. No. 4,741,733.

U.S. Pat. No. 6,569,128 describes a catheter flow restriction system wherein a capillary-like restriction tube is contained within a catheter tube. The flow rate through the system is adjusted by trimming the length of the restriction tube and concentric catheter tube. The catheter can then be attached to an infusion device by a suitable connector, such as a Touhy-Borst connector.

Conventional flow restriction devices are, however, not without certain drawbacks, particularly the capillary tube restrictors. For example, such tube-type devices are relatively difficult and expensive to manufacture. Also, as requirements in the medical field tend towards decreased flow rates, it has become increasingly difficult to manufacture the tubes to achieve a specified flow rate due simply to machining tolerances and material limitations. For example, the smaller (in diameter) the tubes become, the more prone they become to particulate clogging.

A need thus exists in the medical field for a more reliable yet inexpensive flow restrictor that may be used in various systems, such as infusions systems and like devices.

SUMMARY OF THE INVENTION

Objects and advantages of the invention will be set forth in part in the following description, or may be obvious from the description, or may be learned through practice of the invention.

In accordance with the invention, a flow restrictor device is provided that is relatively inexpensive to manufacture and assemble, yet will reliably maintain a precisely regulated flow rate. The device is not prone to clogging, and is easily incorporated into any conventional medical infusion or other type of fluid delivery system. In this regard, it should be appreciated that although the inventive restrictor has particular usefulness in an infusion delivery system, the invention is not limited to this particular application. The inventive restrictor may be used in any system wherein it is desired to restrict or regulate the flow of a fluid, and all such uses are within the scope and spirit of the invention.

The term "fluid" is used herein to refer to a gas, liquid, or combination of a gas and liquid.

The flow restrictor according to the invention includes a housing having an inlet and an outlet, and a fluid path defined through the housing between the inlet and outlet. The inlet and outlet are configured to be connected in-line, for example with tubing or the like, in a medical apparatus, such as an infusion system. The inlet and outlet may be releasably connected to the medical apparatus tubing, for example with a simple press fit, clamp, or fitting, or permanently attached by, for example, by way of an adhesive, ultrasonic bond, a weld, and so forth.

At least one pair of opposed restriction surfaces are provided within the housing between the inlet and outlet. The restriction surfaces are placed in contact against each other and are disposed in the flow path such that fluid delivered to the inlet must pass between the opposing surfaces prior to flowing from the outlet. Any one or combination of seals, such as O-rings, gaskets, or the like, may be used within the housing to establish the desired flow path through the devices. A resilient member, such as a spring, wave spring, or similar device may be used to bias the restriction surfaces together depending on the configuration of the surfaces. Alternatively, the seal may be resilient and also function to bias the restriction devices together.

A pattern of fluid flow passages is defined in one or both of the restriction surfaces as a non-random repeating pattern, such as any defined geometric pattern. For example, the pattern may be a continuous spiral (similar to a screw thread), or a plurality of spirals. In an alternate embodiment, the pattern of fluid flow passages may be a grid defined in one or both of the restriction surfaces.

The pattern of fluid flow passages may be defined in the surface of the restriction surfaces by any conventional process known to those skilled in the art. For example, the pattern may be defined by any one or combination of processes, including machining, etching, cutting, molding, and so forth. It should be appreciated that the invention is not limited by the process for defining the pattern of flow passages.

The pattern of fluid flow passages may have an overall volume (i.e., number, length, cross-sectional area, and so forth) that is pre-determined as a function of a desired volumetric flow rate through the restrictor. The pattern may be determined by a computer-aided design program, or through routine experimentation with varying patterns.

In a particular embodiment, the flow restrictor includes at least one pair of opposed restriction devices seated within the housing, with the restriction surfaces defined on opposing surfaces of the restriction devices. The restriction devices may take on various shapes and be formed from any number of suitable materials, such as glass, ceramic, steel, and so forth. For example, in one particular embodiment, the restriction devices are opposed flat planar members disposed within the housing such that fluid from the inlet flows radially between the opposing surfaces. In one particular embodiment, fluid from the inlet is directed to the outer circumference of the restriction devices and flows radially inward between the opposing surfaces. The bottom (downstream) member has an orifice that defines an exit path for the fluid from between the planar members. The orifice is aligned with, or otherwise in fluid communication with, the housing outlet.

In an alternate embodiment, the upstream restriction device (e.g., an upstream flat planar member) may have an opening or orifice and the flow path within the housing is established such that fluid flows through this orifice and then migrates radially outward between the opposing surfaces prior to flowing to the outlet.

The flat planar member restriction devices may take on various shapes, sizes, thicknesses, etc. In one particular embodiment, the members are circular discs stamped or otherwise formed from a desired material. Such devices may be desired from the standpoint of ease of manufacture and assembly.

It should be appreciated that it is not necessary that each of the opposing restriction surfaces include the pattern of fluid passages defined therein. One of the surfaces may include the pattern, while the other surface is relatively smooth.

The restriction surfaces may be defined in a hard, non-compressible material, such as a medical grade stainless steel, so that fluid flow between the opposing restriction surfaces is substantially constant regardless of a compressive pressure applied to the surfaces from fluid pressure or assembly of the housing components. In an alternate embodiment, the restriction surfaces may be defined in a compressible material, such as a medical grade polymer material, so that fluid flow between the opposing surfaces may be changed or adjusted by varying a compressive pressure applied to the restriction surfaces, for example by way of housing components that may be threadedly engaged.

In one particular embodiment, the restriction surfaces may be defined between a conical male member that mates within a complimentary shaped recess such that the opposing restriction surfaces are defined by the conical wall of the male member and the recess wall. The conical member may have straight sides (i.e., constant slope) or curved sides. This embodiment may be desired in that a larger surface area between the opposing restriction surfaces may be achieved, thus permitting a greater degree of metering or fluid restriction.

In yet another embodiment, the restriction surfaces may be defined by a ball member seated within a ball seat such that the opposing restriction surfaces are defined by a circumferential portion of the ball member and the ball seat. One or both of these surfaces will have the pattern of fluid flow passages defined therein.

In the embodiment utilizing restriction devices, the housing may include separate halves, with the restriction devices being placed within the halves prior to joining the halves to form the complete housing. The halves may be separable after being joined for access to the restriction devices. For example, the halves may be threaded onto each other, or otherwise releasably engaged. Alternatively, the halves may be permanently joined, for example by way of an adhesive, weld, and so forth.

The restriction devices may be variously oriented within the housing relative to the inlet and outlet. For example, in one embodiment, the devices are disposed such that a plane between the opposing surfaces is generally perpendicular to an axis of the inlet and outlet. In an alternate embodiment, the restriction devices are disposed such that the plane between the opposing surfaces is generally parallel to an axis of the inlet and outlet.

In an alternate configuration of a flow restrictor device in accordance with the invention, the opposed flow restriction surfaces may be defined directly on opposed surfaces of the housing members. For example, a first flow restriction surface may be formed as an integral surface on an inlet housing member, and a second flow restriction surface may be formed as an integral surface of an outlet housing member. Upon mating the inlet and outlet housing members, the respective flow restriction surfaces are opposed and the fluid path through the restrictor flows between the opposed flow restriction surfaces, with the fluid flow being a function of a compressive force between the housing members.

In a particular embodiment, a forward portion of the inlet housing member is received within a recess defined in the outlet housing member. The first opposed flow restriction surface is formed directly on the forward portion of the inlet housing member, and the second opposed flow restriction surface is formed directly in the recess of the outlet housing member. Alternatively, the recess may be formed in the inlet housing member, and the portion received in the recess may be formed on the outlet housing member.

The recess and mating portion may have various shapes and configurations. For example, in one particular embodiment, the forward portion of the inlet housing member comprises a tapered conical configuration, and the recess defined in the outlet housing member has a corresponding tapered conical configuration. In an alternate embodiment, the recess may have a semi-spherical configuration, or a cylindrical configuration with a flat planar flow restriction surface, and the portion received in the recess has a corresponding shape.

The inlet and outlet housing members may be formed of various suitable materials. In a particularly desirable embodiment, one or both of the members are molded from a polymer material such as a medical grade plastic. At least one of the flow restrictions surfaces may be compressible to a degree such that fluid flow through the pattern of passages is changed by varying a compressive pressure applied to the inlet and outlet housing members. In this regard, the portion of the housing member defining the flow restriction surface may be formed of a compressible plastic. Alternately, the housing member or members may be made of a relatively hard non-compressible material with only the flow restriction surfaces being made of a compressible material added to the harder material as a layer, cap, coating, etc.

To ensure that fluid flow through the restrictor is directed between the opposed flow restriction surfaces, a seal such as an O-ring, gasket, and so forth, may be disposed at a suitable location between the inlet and outlet housing members. The inlet and outlet housing members may be mated together by various conventional methods. For example, the members may be glued, bonded, welded, and so forth. The members may be permanently fixed together, or releasably attached.

In a particularly desirable embodiment, the inlet and outlet housing members are molded components, with the pattern of fluid flow passages being defined in the molding process.

As with the other embodiments of the flow restrictor, the inlet and outlets of the housing members may be connectable to tubing in fluid delivery system such that the restrictor is placeable in-line within such a system.

The housing members may be permanently fixed together, for example by use of an adhesive, weld, or any other conventional attaching method depending on the particular type of material used to manufacture the housing members. In a particular embodiment, the housing members are molded plastic components, and an adhesive such as a UV cured adhesive may be used to fix the members together to ensure the desired flow rate is a permanent characteristic of the restrictor.

Alternately, the housing members may be separable. For example, there may be uses of the restrictor in systems wherein flow rates may need to be adjusted or varied without removing the restrictor from the system. Depending on the fluid conducted, certain systems may require the components to be made of relatively expensive corrosion resistant materials wherein it is not economically feasible to discard the restrictors or carry a large inventory of restrictors for various flow rates. It may thus be desired to vary the flow rate through the restrictor by varying the compressive force between the housing members, and thus varying the volume of the fluid flow passages. A threaded connection between the housing members, or other suitable adjustable connection, may be used for this purpose.

The predetermined compressive force used to achieve the desired flow rate may be determined in various ways. For example, the flow rate may be calculated from know variables and geometries related to the housing members, compressibility of the housing member materials, pressure of fluid through the system, and so forth. This calculated compressive force may then be used to assemble the components together, or adjust the flow rate at a later time.

In an alternative embodiment, the compressive force may be empirically determined in a carefully controlled simulation. For example, the components may be assembled in a testing apparatus that measures compressive force and flow rate through the restrictor as the compressive force is applied. Thus, flow rate as a function of compressive force may be readily determined for housing members of a given geometry, material, etc. The testing apparatus may be implemented with computer controls and analysis for precisely applying, varying, and measuring compressive pressure, as well as flow rate through the restrictor.

It should be readily apparent to those skilled in the art that such a testing apparatus may be configured in numerous ways, and with various types of commercially available equipment, or machinery configured specifically for the desired purpose.

The invention also encompasses any manner of medical fluid delivery system that incorporates one or more of the unique fluid restriction devices as described herein.

The invention will be described in greater detail below by reference to particular embodiments shown in the referenced figures.

DETAILED DESCRIPTION

Reference will now be made in detail to examples of the invention, one or more embodiments of which are illustrated in the figures. Each example is provided by way of explanation of the invention, and not meant as a limitation of the invention. For example, features illustrated or described as part of one embodiment may be used with another embodiment to yield still a further embodiment. It is intended that these and other modifications and variations be included within the scope and spirit of the invention.

Figure 1A:
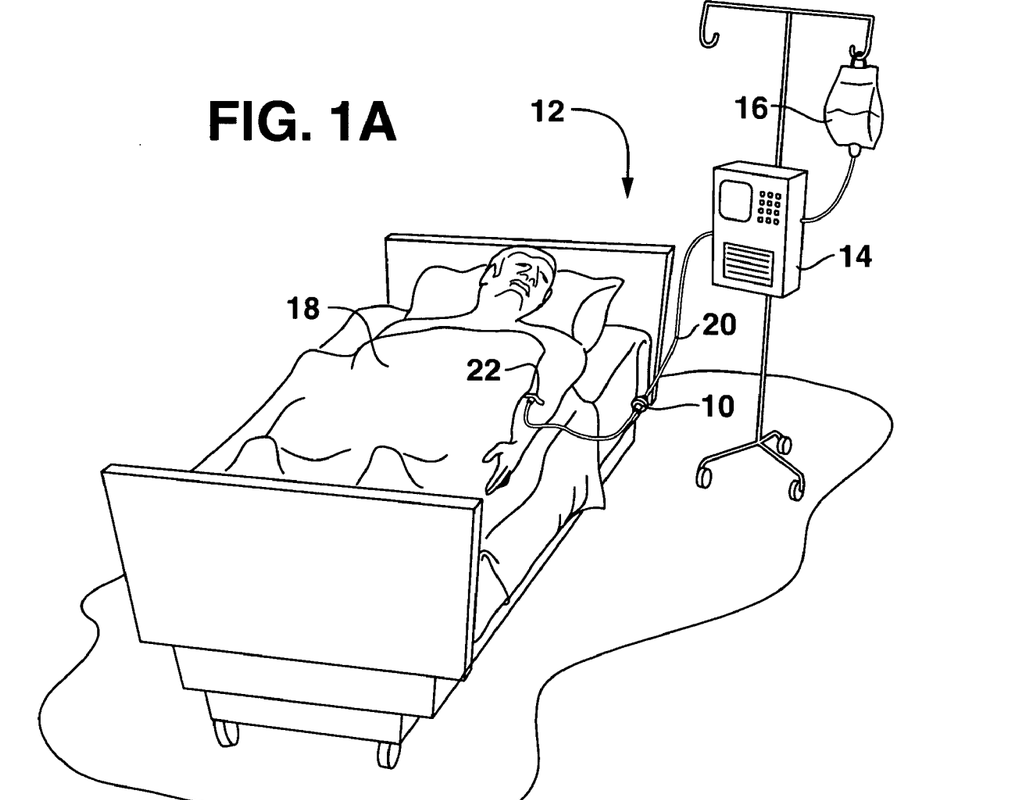
FIG. 1A is a perspective view of a conventional infusion pump system incorporating a flow restrictor according to the invention.

FIG. 1A illustrates an embodiment of a medical system, generally 12, that may utilize a flow restrictor 10 according to the invention. The medical system 12 is illustrated as a conventional infusion system wherein an infusion pump 14 is supplied with a fluid, such as a medicine, by a solution container 16 that is supported at a given height above the pump 14. Tubing 20 supplies the fluid from the pump 14 to an intravenous (IV) site 22 on a patient 18. Such infusion systems and pumps 14 are well known by those skilled in the medical art. Such systems are supplied, for example, by Braun Medical, Inc. of Bethlehem, Pa., and Baxter Healthcare Corporation of Round Lake, Ill. The flow restrictor 10 is illustrated as connected in-line in the tubing 20 between the pump 14 and the patient 18. It should also be appreciated that the restrictor 10 may be incorporated within the housing of the pump 14.

Figure 1B:
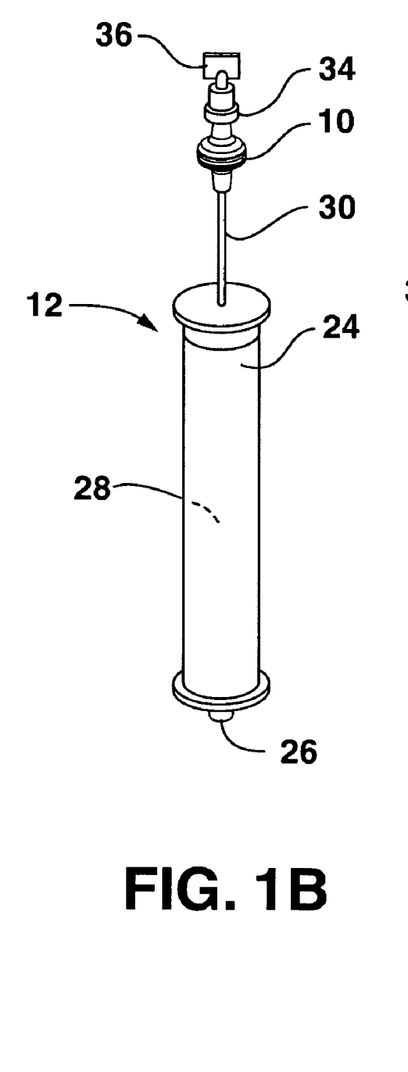
FIG. 1B is a perspective view of a conventional portable medical infusion system incorporating a flow restrictor according to the invention.
Figure 1C:
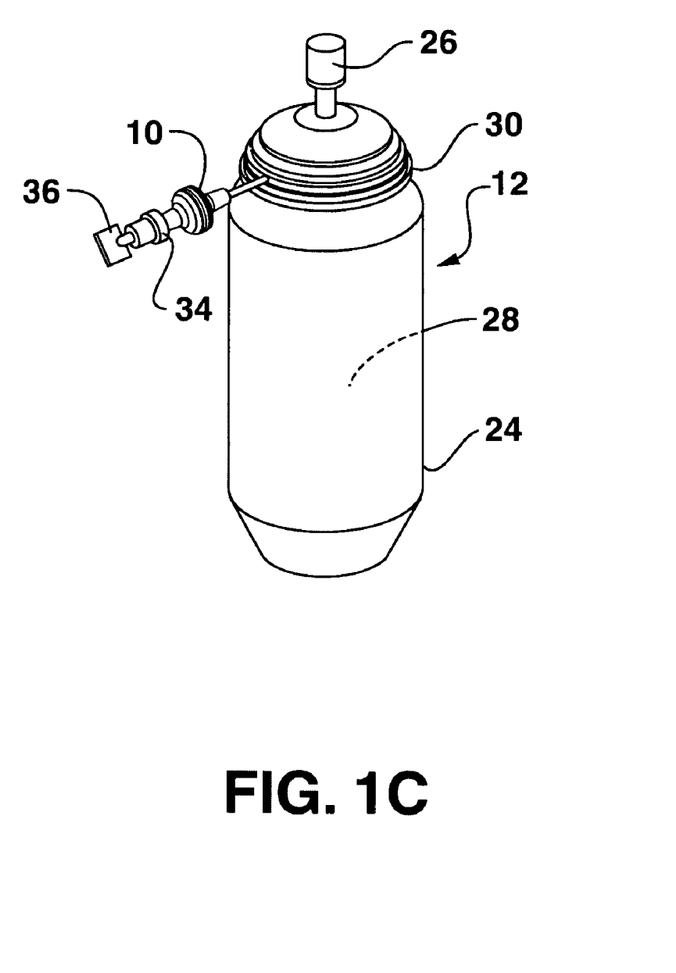
FIG. 1C is a perspective view of yet another conventional medical infusion system incorporating a flow restrictor according to the invention.

FIGS. 1B and 1C illustrate portable infusion systems that are generally worn or carried by a patient. Such devices are commercially available, for example, from Baxter Healthcare Corporation. FIG. 1B illustrates a small-volume system wherein a housing 24 defines an internal reservoir 28. A flexible membrane, such as an elastomeric balloon or the like, is contained within the reservoir 28 and provides fluid pressure. A fill port and associated cap 26 are provided for filling the reservoir 28. Delivery tubing 30 connects the housing 24 to a delivery end connector 34, such as a conventional luer connector. A cap 36 is provided for the connector 34. A flow restrictor 10 in accordance with the invention is provided in-line in the tubing 30 between the connector 34 and the housing 24. The connector 10 may be removably connected in the tubing 30, or permanently attached in the tubing 30, as described in greater detail below.

The infusion device of FIG. 1C is similar to that of FIG. 1B, but includes a larger housing 24 and internal reservoir 28. The reservoir 28 also includes an elastomeric "balloon" type of member for holding the fluid medication under sufficient pressure for delivery to the patient.

Although described with reference to infusion-type systems, it should be readily appreciated that the flow restrictor 10 according to the invention may be used in any medical system wherein it is desired to deliver a metered amount of a fluid to a patient from a pressurized source. For example, the restrictor 10 according to the invention can be utilized for continuous or intermittent delivery of fluids through clinically acceptable routes of administration, such as intravenous (IV), intra-arterial (IA), subcutaneous, epidural, or irrigation of fluid spaces applications.

Figure 2:
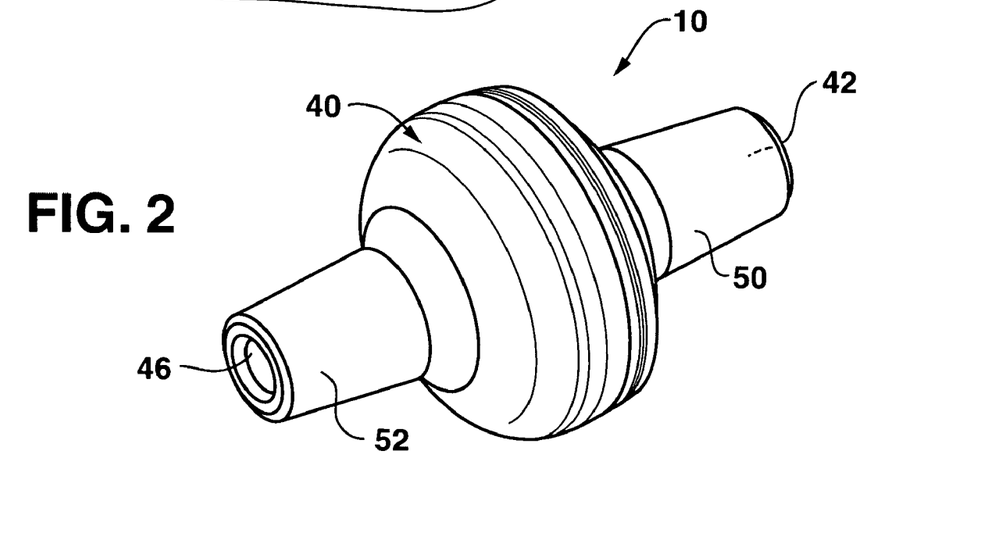
FIG. 2 is a perspective view of an embodiment of a flow restrictor according to the invention.

FIG. 2 illustrates an embodiment of the flow restrictor 10 in accordance with the invention. The restrictor 10 includes a housing 40 that may take on generally any desired shape or design. The housing 40, in one particular embodiment, is defined by separate halves or elements 50, 52, as described in greater detail below. The flow restrictor 10 includes an inlet 42 through which fluid is introduced into the device 10, and an outlet 46 from which fluid is conducted after flowing through the device 10.

Referring to FIGS. 3A through 3C, 4A, and 4B, an embodiment of the flow restrictor 10 of FIG. 2 is illustrated in greater detail. In this embodiment, the flow restriction surfaces are defined on separate restriction devices seated in the housing 40, as discussed in greater detail below. The housing 40 includes a first half 50 and a second half 52. The first half 50 defines the inlet 42 and an inlet passage 44. Similarly, the second half 52 defines an outlet passage 48 and the outlet 46. The halves 50, 52, may be configured to be releasably attached to medical tubing, for example by way of a clamp, or a simple friction or press fit of the tubing over the elongated ends of the respective halves 50, 52. Alternately, the tubing may be permanently attached to the respective halves 50, 52, by an adhesive, weld, or any other suitable permanent attachment means.

Figure 3A:
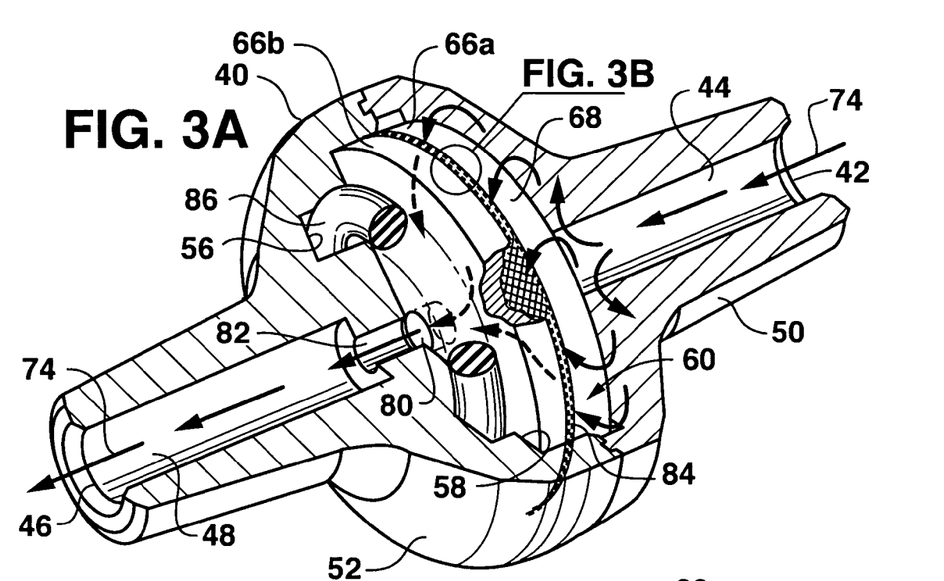
FIG. 3A is a cross-sectional view of the flow restrictor of FIG. 2, particularly illustrating the flow path for a fluid through the device.
Figure 3B:
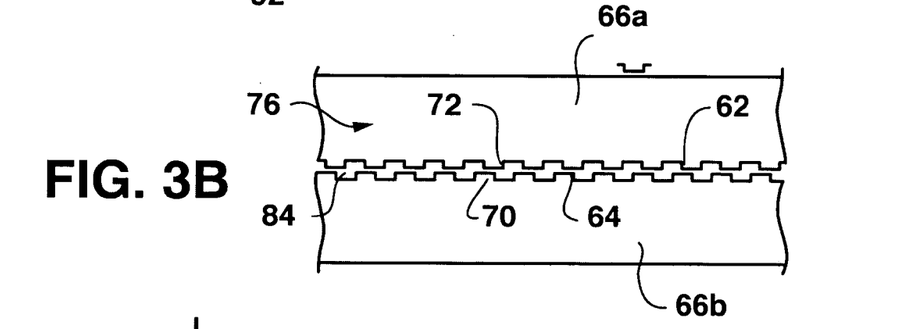
FIG. 3B is an enlarged view of the section of the circumference of the flow restriction devices indicated in FIG. 3A.
Figure 3C:
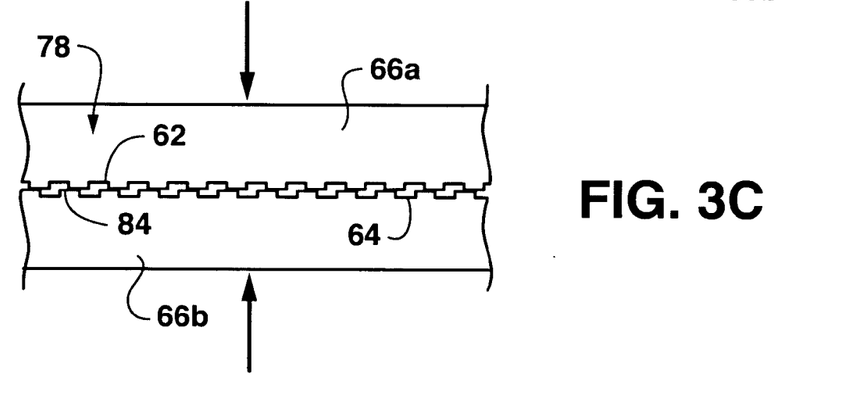
FIG. 3C is a side view of an embodiment of compressible flow restriction devices.

At least one pair of opposed restriction devices 60 are seated within the housing 40 between the inlet 42 and the outlet 46. The restriction devices 60 may take on various forms, so long as they define opposed restriction surfaces 62 and 64 placed in contact against each other such that a patterned restrictive flow field 84 is defined between the opposed surfaces. For example, in the embodiment illustrated in the figures, the restriction devices 60 are defined by generally flat planar members 66a and 66b disposed against each other. The planar members may take on any shape, and in the figures are depicted as circular disks contained in the housing 40 by way of disk seats 58. Referring particularly to FIGS. 3A and 3B, it can be seen that both of the disks 66a or 66b includes a defined geometric pattern of fluid flow passages such that when the opposing surfaces 62 and 64 are placed against each other, a restrictive fluid flow field 84 is defined between the surfaces. In the illustrated embodiment, each of the disks 66a and 66b includes a grid pattern of fluid flow passages 72 and 70 defined therein such that each of the opposed surfaces 62 and 64 contributes to the total volume of the restrictive flow field 84, as particularly seen in FIG. 3B. It should be appreciated that the passages 72 and 70 are grossly exaggerated in the figures for purposes of illustration only. It may very well be that, for many embodiments, the passages are not discernible by the unaided eye.

By carefully controlling the geometry and number of the passages 72 and 70, the rate of fluid flow between the opposed restriction surfaces may be controlled with relative precision to achieve a desired flow rate through the device 10. For a specific fluid pressure, a desired fluid flow rate can be achieved by carefully defining the particular parameters of the passages 72 and 70 and overall surface area of restrictive flow field 84. Taking these factors into consideration, the restriction devices 66a and 66b may be designed for a particular flow rate based on prediction algorithms, or determined empirically through routine experimentation.

The cylindrical disk-type restriction devices 66a, 66b, may be desired in that they are relatively inexpensive and easy to fabricate. For example, the components may be punched, stamped, turned, and so forth. The fluid flow passages 70 and 72 may be defined in the same processing step, or in a subsequent step. The pattern may be defined by any conventional method, including but not limited to, molding, etching, machining, cutting, grinding, and so forth.

In the embodiment illustrated in FIGS. 3A and 3B, the restriction devices 66a, 66b, are formed from a relatively incompressible, hard material, such as stainless steel, glass, ceramic, and so forth. In this manner, the cross section of the flow passages 70, 72 is predominantly unchanged or unaltered by the degree of compression of the devices against each other. Alternatively, it may be desired that the devices 66a, and 66b, are formed from a compressible material, such as a relatively soft poly material. In this manner, the cross section of the passages 70, 72 changes with compression of the devices 66a, 66b and the restrictive flow field 84 may be made more or less restrictive depending upon the degree of compression of the components 66a, 66b, against each other, as is diagrammatically illustrated in FIG. 3C. The "soft" disks 66a, 66b, may be used in an embodiment wherein the housing halves 50, 52, are relatively adjustable relative to each other, for example as in a threaded engagement between the two halves. With this configuration, different flow rates may be achieved with a single restrictor 10, or the restrictor may be adjusted or fine-tuned for achieving a very accurate flow rate.

Figure 4A:
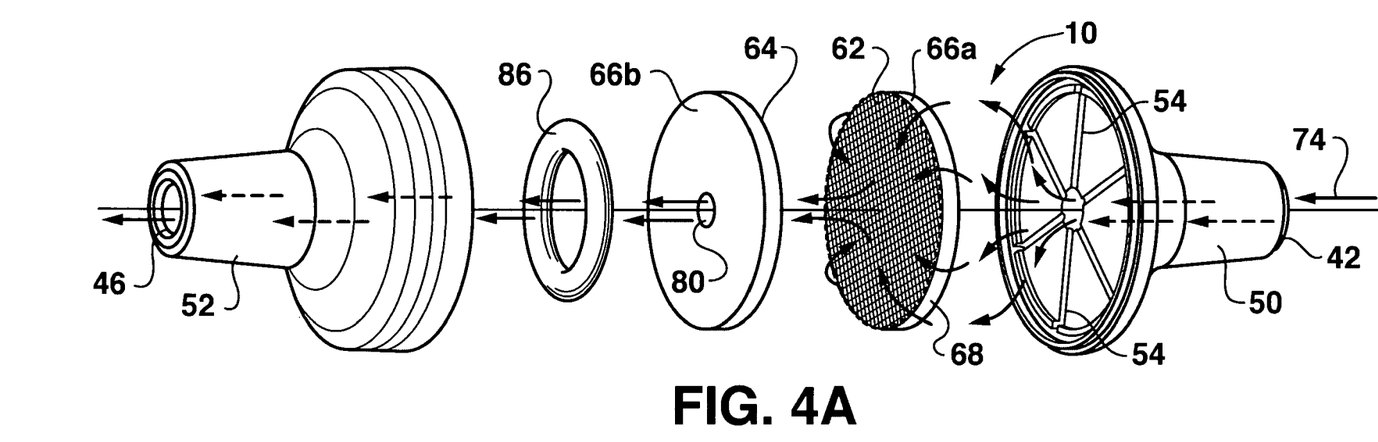
FIG. 4A is an in-line component view of an embodiment of the flow restrictor particularly illustrating the fluid flow path from the inlet to the outlet.
Figure 4B:
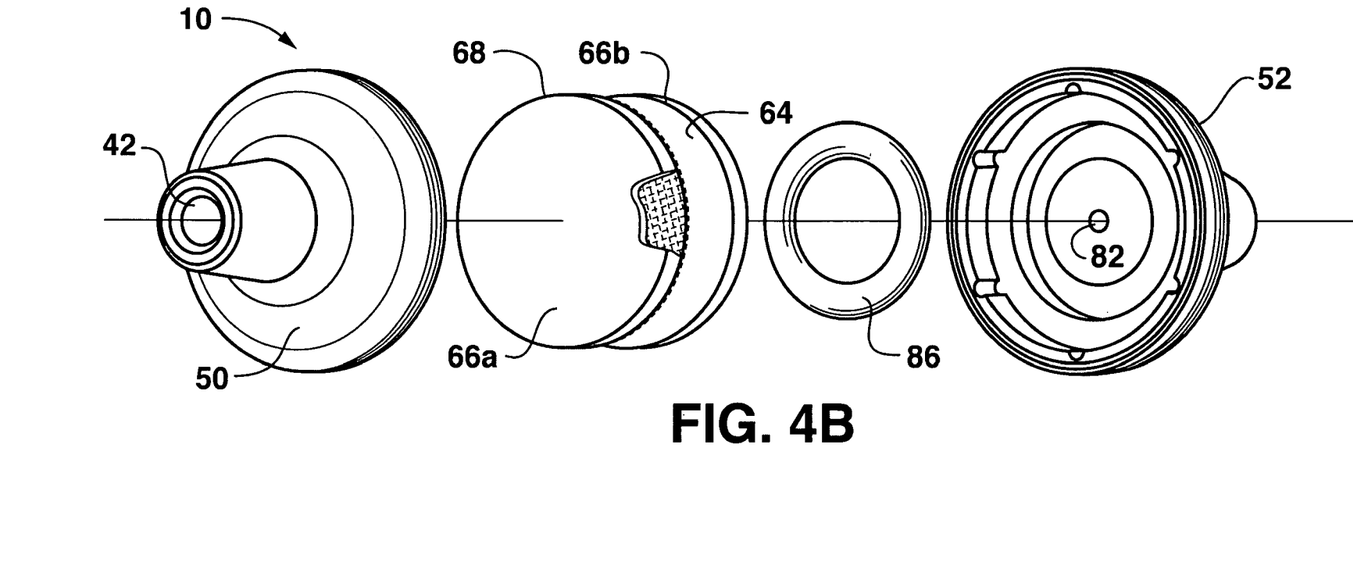
FIG. 4B is an in-line component view of the embodiment of FIG. 4A taken from the opposite direction.

FIGS. 4A and 4B illustrate an embodiment of a restrictor 10 wherein a grid pattern of fluid flow passages is defined on the restriction surface 62 of disc 66a, and the opposed restriction surface 64 of disc 66b is smooth. Fluid moves under pressure in a flow path 74 through the inlet 42 and inlet passage 44 and is directed to the perimeter or circumference 68 of the restriction devices 66a, 66b, by way of relief channels 54 or other suitable structure defined in the housing half 50. A sealing device 86, such as a conventional O-ring, gasket, or any other suitable elastomeric sealing device, is disposed in a seat 56 in the housing second half 52, as particularly seen in FIG. 3A. This seal 86 prevents the fluid from bypassing the restrictive field 84. Referring particularly to FIG. 3A, it can be seen that the fluid migrates from the circumference of the restriction devices 66a, 66b radially inward at a rate that is defined as a function of the overall volume of the restrictive flow field 84 between the opposed surfaces 62, 64, of the restriction devices, as discussed above. The fluid migrates to an orifice 80 defined in the downstream restriction device 66*b*. The orifice 80 is in fluid communication with the outlet passage 48, for example by way of an orifice passage 82.

It should be appreciated that any number of configurations of internal structure, sealing devices, and so forth, may be utilized within a housing 40 to ensure that fluid is directed through the restrictive field 84 of opposed restriction devices 66*a*, 66*b* to disburse the fluid from the outlet 46 at a desired flow rate. It may be desired to incorporate the sealing element in the housing, for example by way of a two-shot injection molding process wherein the second shot is an elastomer. Alternatively, a sealing element may be provided on one or both of the disks 66*a*, 66*b* (or other type of restriction devices). For example, the disks 66*a*, 66*b* may be stamped from a composite metal/rubber sheet wherein the metal component defines an opposing surface of the restriction device, and the rubber component defines the seal. In still an alternative embodiment, the seal need not be elastomeric. For example, the seal may be defined by an epoxy, glue, or ultrasonic bond between the disk and a housing member.

It should be appreciated that the fluid flow passages need not be defined in each of the opposing surfaces 62 and 64. It should be appreciated that the invention also includes the configuration wherein only one of the surfaces 62, 64 has the pattern of fluid flow passages defined therein, as discussed above with respect to the embodiment of FIGS. 4A and 4B. In other words, the restrictive flow field 84 may be achieved by opposed surfaces wherein one of the surfaces is relatively smooth or polished with respect to the other surface. Alternatively, for ease of manufacturing, assembly, and so forth, it may be desired that all of the components are essentially the same and axis-symmetric. For example, if both sides of the restriction disk 66*a*, 66*b* are machined with the pattern of fluid flow passages, then assembly is facilitated by eliminating a particular surface to surface orientation. This design is optimized for pick-and-place automated assembly.

It should also be appreciated that, for varying flow rates, several restrictive devices 66*a*, 66*b* may be stacked within a common housing.

The halves of the housing 40 may be releasably attached to each other after insertion of the sealing device 86 and restriction devices 66*a*, 66*b*, or permanently attached to each other. For example, the halves, 50, 52, may be threadedly engaged such that the device 10 may be subsequently taken apart for replacement of the restriction devices 66*a*, 66*b*. In an alternative embodiment, the halves 50, 52 may be permanently adhered to each other with an adhesive, ultrasonic bonding, welding, or any other conventional attaching means.

Figures 5, 6:
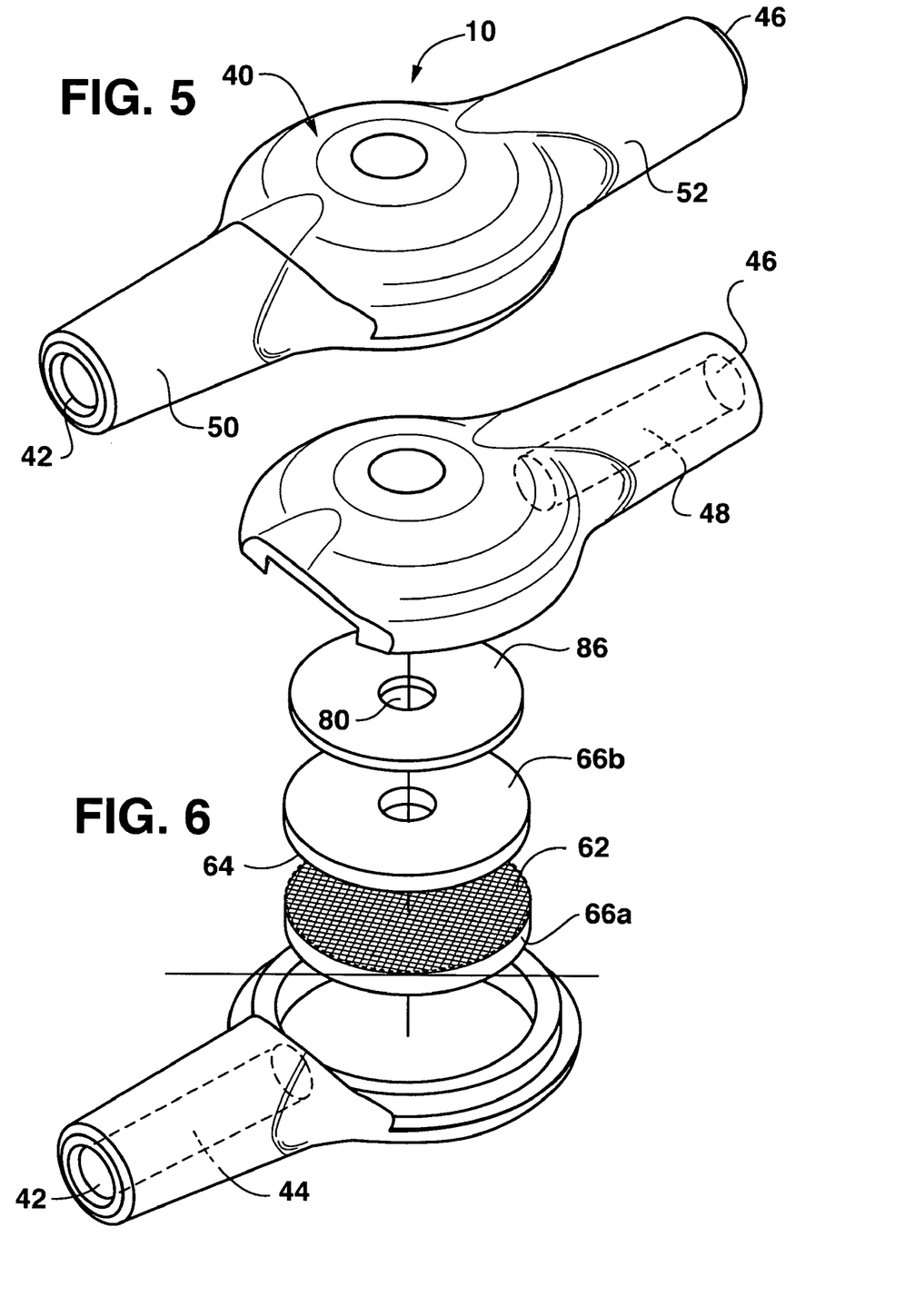
FIG. 5 is a perspective view of an alternate embodiment of a flow restrictor according to the invention.
FIG. 6 is a component view of the embodiment of FIG. 5.

It should also be appreciated that the restriction devices 66*a*, 66*b*, may be variously oriented within the housing 40. For example, in the embodiment illustrated in FIGS. 3A, 4A, and 4B, the devices 66*a* and 66*b* are oriented such that a plane between the opposing surfaces 62, 64, is generally perpendicular to the axis of the inlet and outlet of the housing 40. FIGS. 5 and 6 illustrate an alternative embodiment wherein the restriction devices 66*a*, 66*b*, and seal 86 (gasket) are oriented within the housing 40 such that the plane between the restriction devices is generally parallel to the axis of the inlet and outlet of the housing 40. Regardless of the orientation of the restriction devices 66*a*, 66*b*, the operation of the device is essentially as described above with reference to the embodiment of FIGS. 3A and 4A, and 4B.

Figure 7:
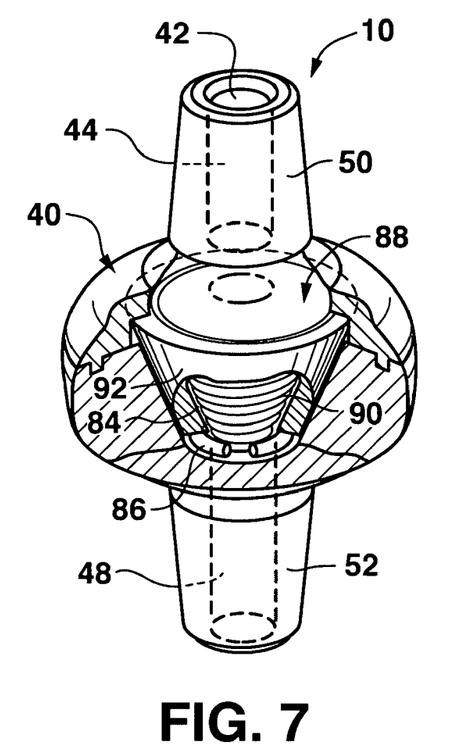
FIG. 7 is a perspective and partial cut-away view of an alternative embodiment of a flow restrictor according to the invention utilizing conical restriction devices.

It should also be appreciated that the restriction devices may take on various shapes and configurations, and include various patterns of fluid flow passages. For example, in the embodiments of FIGS. 7 and 8, conical restriction devices 88 are provided. A conical or truncated male member 90 has a pattern of fluid passages defined on the outer surface in the form a threaded surface, or a continuous spiral configuration. The male member 90 is seated within a correspondingly shaped recess of an opposite member 92 having a smooth surface opposed to the threaded surface pattern in the male member 90. The restrictive flow path is thus defined between the conical walls of the members 90 and 92, wherein only one of these opposed surfaces includes a pattern of fluid flow surfaces defined therein. In the embodiment of FIG. 7, the conical opposed surfaces are relatively straight in that they have a constant slope.

Figure 8:
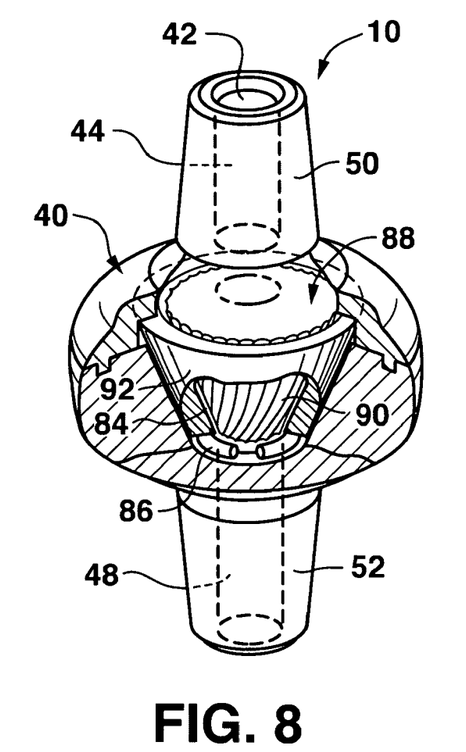
FIG. 8 is a perspective and partial cut-away view of an alternative embodiment of a flow restrictor according to the invention utilizing conical restriction devices having radially curved side walls.

In the embodiment of FIG. 8, the opposed conical surfaces are curved, or have a radial component along at least a portion thereof. The pattern of fluid flow passages in defined on the surface of the male member 90 as a plurality of distinct spirals, and not a single continuous spiral. The embodiments of FIGS. 7 and 8 provide for an increased surface area between the opposed surfaces defining the restrictive flow field 84, as compared to the flat disk devices 66*a*, 66*b*, of the prior embodiments.

Figure 11:
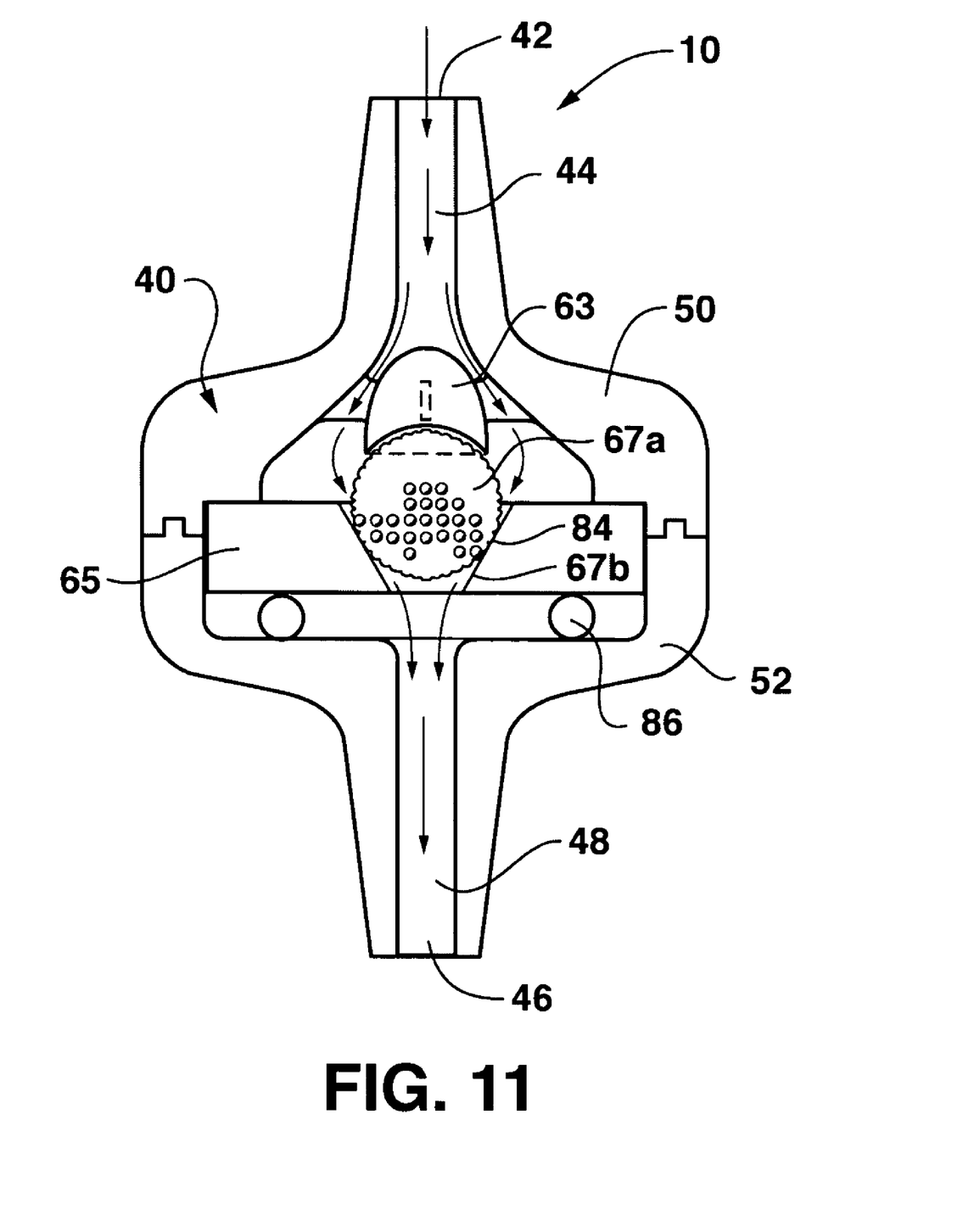
FIG. 11 is a cross-sectional diagrammatic view of an embodiment of a flow restrictor wherein the restriction devices include a ball seated within a ball seat.

FIG. 11 illustrates an embodiment of a flow restrictor 10 wherein the restriction devices are defined by a ball member 67*a* and a planar member 65 having a ball seat 67*b* defined therein. The restrictive fluid flow path 84 is defined between the circumferential portion of the ball member 67*a* and surface of the ball seat 67*b*. Either one or both of the ball surface or ball seat may include a pattern of fluid flow passages defined therein. In the illustrated embodiment, the surface of the ball member includes a pattern of raised projections such that a fluid flow path is defined between the projections. A flow distributor 63 may be incorporated within the housing as an integrally formed or separate component. The distributor 63 may take on any shape to direct fluid from the inlet passage 44 to the restrictive fluid flow path 84 and may also serve to positively engage and contain the ball 67*a* within the ball seat 67*b*. This embodiment may be desired from the standpoint of cost and ease of manufacture.

It should be appreciated that various configurations of restrictive devices may be derived empirically or otherwise by those skilled in the art to define a restrictive flow field 84 between opposed surfaces in accordance with the principles of the present invention.

Figure 9:
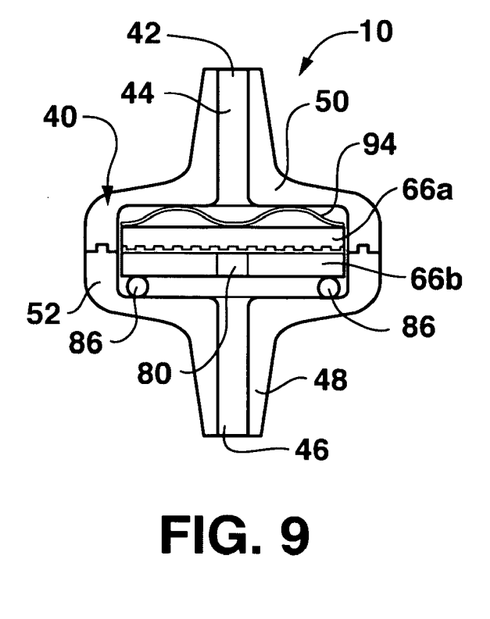
FIG. 9 is a cross-sectional diagrammatic view of an alternate embodiment of a flow restrictor incorporating a biasing element with the housing.

FIG. 9 illustrates an embodiment of a restrictor 10 incorporating a resilient biasing element within the housing 40. The biasing element may be in the form of a wave spring 94 as illustrated in the FIG. 9, or may be any other conventional biasing element such as a spring, and so forth. The biasing element serves to ensure that the restriction devices 66*a*, 66*b* are biased together so that the opposing surfaces properly define the desired restrictive flow path 84. It should also be appreciated that the sealing element 86 in the embodiments of FIG. 3*a* and FIG. 11, for example, may be formed of an elastomeric material and may also serve the function of biasing the restriction devices together.

Figure 10:
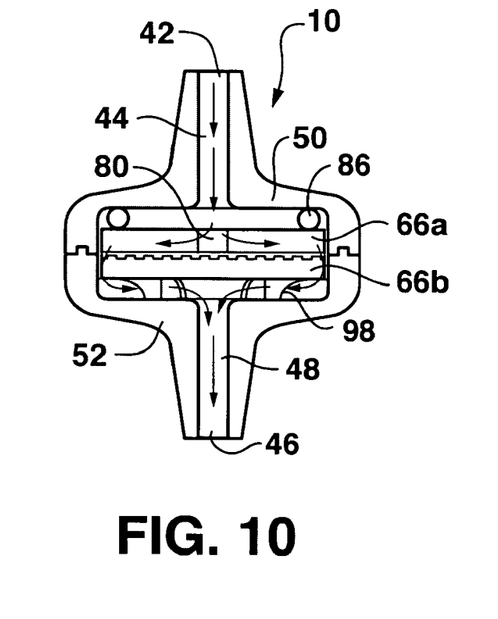
FIG. 10 is a cross-sectional diagrammatic view of an embodiment of a flow restrictor having a flow path such that fluid flows radially outward between the opposed surfaces of the restriction devices.

FIG. 10 is an embodiment of a restrictor 10 wherein the fluid flows in a radially outward direction along the restrictive flow path 84 between the restriction devices 66*a*, 66*b*. An orifice 80 is defined generally at the center of the upstream restriction device 66*a*. The sealing device (ring) 86 is disposed concentric about the orifice 80 such that fluid entering from inlet passage 44 is caused to flow through the orifice 80 to the restrictive flow path defined by the opposing surfaces of the restriction devices 66*a*, 66*b*. The fluid then flows radially outward along the flow path, as indicated by the arrows in FIG. 10, and around the periphery of the downstream restriction device 66b where it is directed to the outlet passage 48. Ridges 98, or any other suitable support structure, are provided within the housing to support the restriction device 66b and define a flow path for the fluid to the outlet passage 48.

In the embodiments of FIGS. 9 and 10, any suitable pattern of fluid flow passages is defined on one of the opposing surfaces of the discs 66a and 66b. The same or a different pattern may also be defined in the opposite surface.

FIGS. 12 through 15 illustrate various other embodiments of restrictors 100 according to the invention wherein opposing flow restriction surfaces are defined directly on mated housing members. For example, a first flow restriction surface may be formed as an integral surface on an inlet housing member, and a second flow restriction surface may be formed as an integral surface of an outlet housing member. One or both of the flow restriction surfaces may include a pattern of fluid flow passages defined therein. Upon mating the inlet and outlet housing members, the respective flow restriction surfaces are opposed and the fluid path through the restrictor flows between the opposed flow restriction surfaces, with the fluid flow being a function of a compressive force between the housing members. It should be appreciated that much of the discussion set forth above with respect to FIGS. 1 through 11 applies equally to the embodiments of FIGS. 12 through 15 and need not be repeated.

Figure 12:
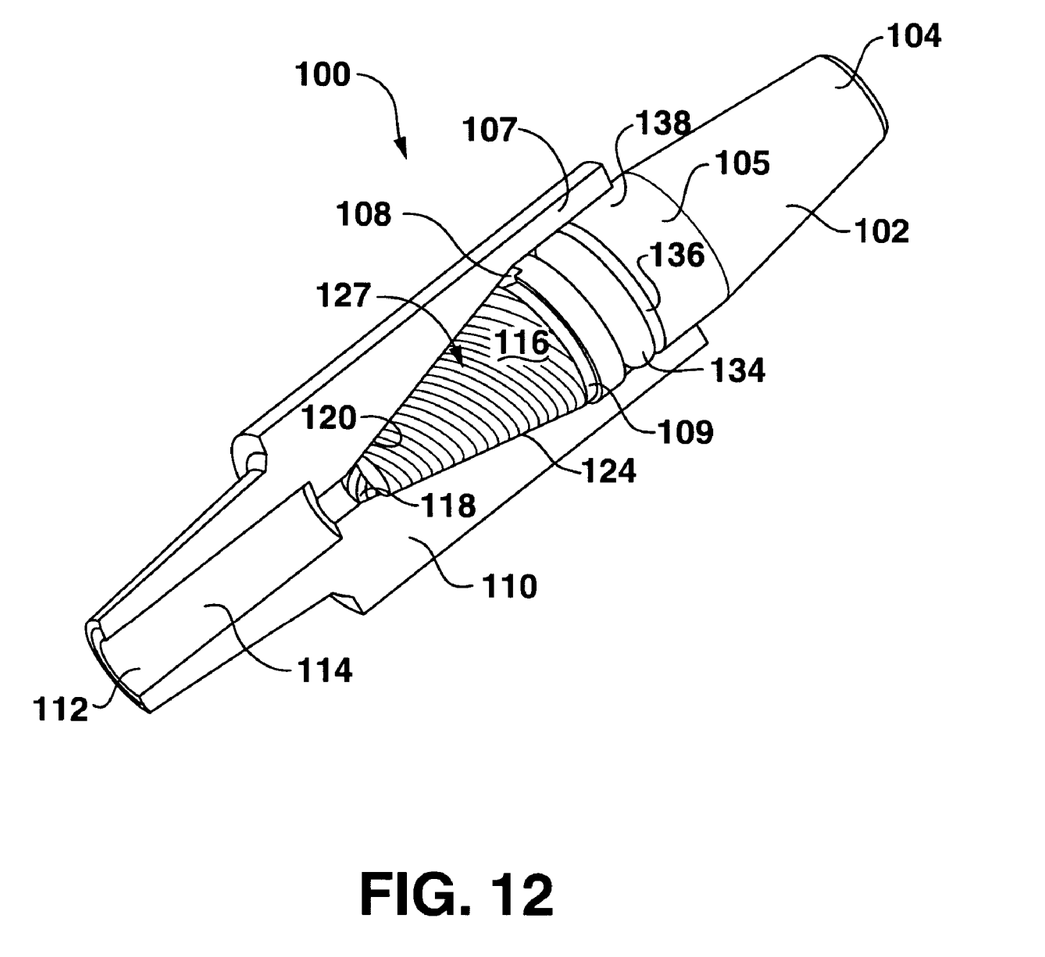
FIG. 12 is a cross-sectional view of an alternate preferred embodiment of a flow restrictor according to the invention.
Figure 13:
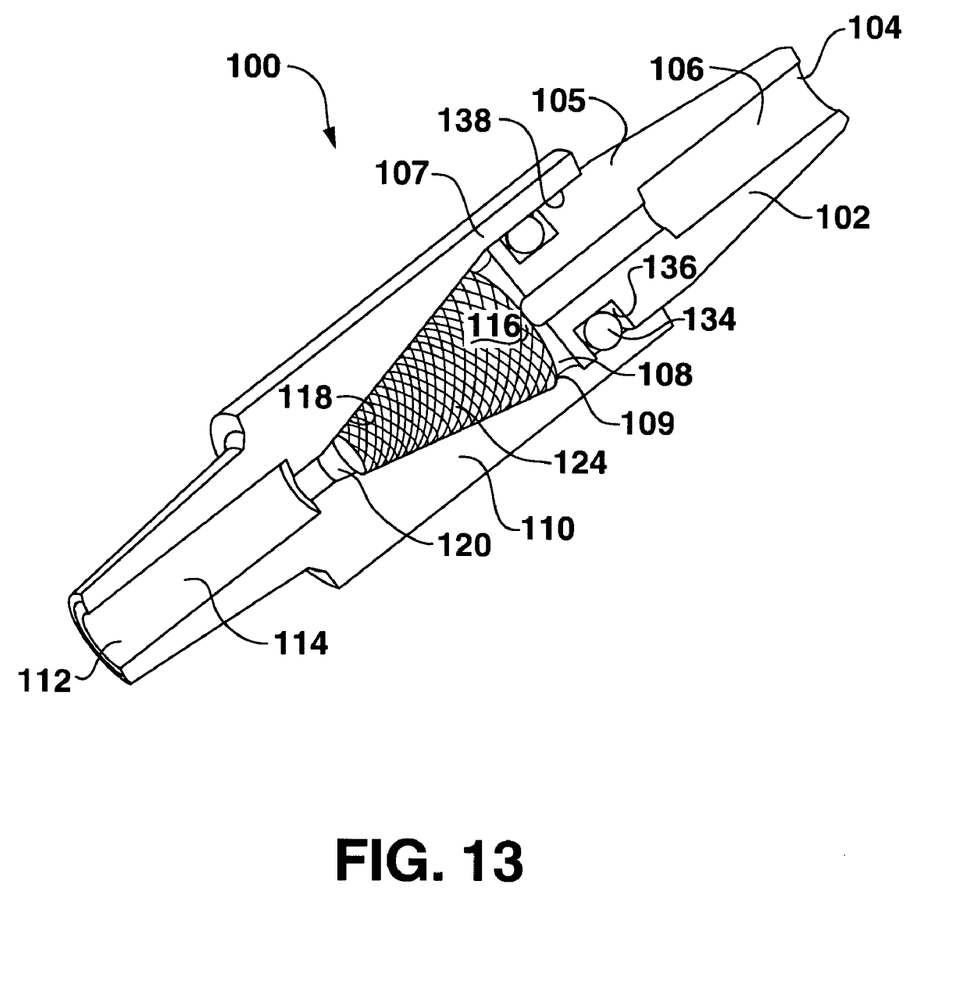
FIG. 13 is a more detailed cross-sectional view of the embodiment of the restrictor of FIG. 12.

Referring to FIGS. 12 and 13 in particular, a flow restrictor 100 includes an inlet housing member 102 and an outlet housing member 110 shown in their mated configuration. The housing members 102, 110 may take on any desired shape and appearance so long as a fluid flow path is defined between an inlet and an outlet of the restrictor 100. In the illustrated embodiment, the inlet housing member 102 is a generally elongated member defining an inlet opening 104, a passage 106, and a forward portion 105. Similarly, the outlet housing member 110 is an elongated member defining an outlet 112, a passage 114, and a receiving portion 107 that mates with the forward portion 105 of the inlet housing member 102.

Opposed flow restriction surfaces are formed on respective surfaces of the inlet and outlet housing members 102, 110 such that a portion of the fluid flow path through the restrictor is defined between the flow restriction surfaces. For example, in the embodiment of FIG. 12, a first flow restriction surface 116 is provided as the surface of a protrusion 124 of the inlet housing member 102, and includes a threaded or spiral fluid passage pattern. An opposed second flow restriction surface 118 is provided on the surface of a recess 120 defined in the outlet housing member 110. The recess 120 has a shape corresponding to the shape of the protrusion 122 and includes a threaded fluid passage pattern having an opposite pitch as compared to that on the surface 116. It should be appreciated that the protrusion 124 may be provided on the outlet housing member 110, and the recess 120 defined in the inlet housing member 102.

In the embodiment of FIG. 13, restriction surface 118 defining the recess 120 is smooth or flat, and the restriction surface 116 on the conical protrusion 124 includes a grid or cross-hatch pattern of fluid flow passages.

Referring to FIG. 13, fluid flowing through the restrictor 100 enters the inlet 104, travels internally along the passage 106, and migrates radially outward along the radial passage 108. The fluid then enters a circumferentially extending relief channel 109. From the channel 109, the fluid must migrate along the tortuous flow path defined by the fluid flow passages between the opposed flow restriction surfaces 116, 118, before entering the outlet passage 114 and exiting the restrictor 100 through the outlet 112. Compression of the opposed flow restriction surfaces 116, 118 is the controlling factor in setting a desired flow rate through the restrictor 100.

The flow restriction surfaces 116, 118 may be defined as an integral surface of their respective housing members. For example, the surfaces 116, 118 may be directly molded with the housing members with a pattern or grid of flow passages molded directly therein. Alternatively, the desired pattern of flow passages may be formed in a subsequent fabrication step. The opposed flow restriction surfaces 116, 118 may have the same or different patterns, or a pattern may be provided on only one of the surfaces.

It is also within the scope of the invention to form the housing members 102, 110 of different materials, wherein the flow restriction surfaces 116, 118 are defined in a material that is different from the remaining portion of the housing member. For example, the housing members 102, 110 may be formed from a composite material wherein the portion defining the flow restriction surface is a plastic material, and the remainder of the housing member is metal. Alternatively, the flow restriction surfaces 116, 118 may be defined on members that are subsequently attached to separately formed components to define a complete housing member. Any number of configurations and combinations of materials are possible.

The recess 120 and mating protrusion 122 may have various shapes and configurations. For example, in the embodiment of FIGS. 12 and 13, the protrusion 122 is a tapered conical member, and the recess 120 is a correspondingly shaped tapered recess. The tapered configuration may be desired in that, if the angle of taper is selected correctly, the housing members 102, 110 become essentially self-locking, which decreases reliance on a subsequent bonding step. The taper angle should be essentially at or slightly below the self-clinching angle for the given material used to form the housing members 102, 110. For example, for polycarbonate materials, the self-clinching angle is approximately 15 degrees (30 degree included angle). Additionally, the taper converts the majority of applied stress into "hoop" stress, which is advantageous from structural and stability considerations.

As the relative degree of compression of the opposed flow restriction surfaces 116, 118 establishes the desired flow rate, the flow restriction surfaces 116, 118 are formed in materials that have at least some degree of relative compression when the housing members 102, 110 are pressed together. The surfaces 116, 118 may be formed of the same materials and thus have the same degree of compressibility, or be formed of different materials and have different degrees of compressibility. In a preferred embodiment, the housing members 102, 110 and their respective flow restriction surfaces 116, 118 are formed of the same polymer material, such as a medical grade polycarbonate. It should be readily understood that the particular material selected is a function of the environment in which the restrictor 100 is intended. For example, in medical chemotherapy applications, plastic materials that are resistant to chemotherapy drugs are desired.

Referring again to FIGS. 12 and 13, a seal 134 is provided between the inlet and outlet housing members 102, 110. This seal 134 may be any conventional sealing device, such as an O-ring, gasket, mechanical seal, and so forth. The seal 134 is desirably an inert material that will not react with the fluid flowing through the restrictor 100. In the illustrated embodiment, the seal 134 is disposed in a recess 136 defined around a portion of the inlet housing member 102 that mates within the receiving portion 107 in the outlet housing member 110. In this position, the seal 136 prevents fluid from flowing out from between the mated housing members. The seal 136 also aids in sealing the housing members 102, 110 during a telescoping assembly process wherein flow rate is fine tuned by adjusting the degree of compression of the housing components 102, 110.

It may also be desired to permanently fix the housing members 102, 110 together to "set" the degree of compression of the opposed flow restriction surfaces 116, 118. This may be accomplished in various conventional ways, including adhesives, welds, and so forth. In a particular embodiment, a UV-cured adhesive may be applied to a mating section of the housing members, such as along the longitudinally extending region 138 between the forward portion 105 of the inlet housing member 102 and the receiving section 107 of the outlet housing member 110. The UV adhesive allows for relative adjustment between the housing members until such time as the mated members are exposed to UV light to cure the adhesive.

In an alternative embodiment, it may be desired to nonpermanently set the relative position of the housing members 102, 110 so that the members can be subsequently adjusted, or even separated. For example, a threaded connection, press-fit or compression connection may be used to allow for subsequent relative movement between the housing members.

Figure 14:
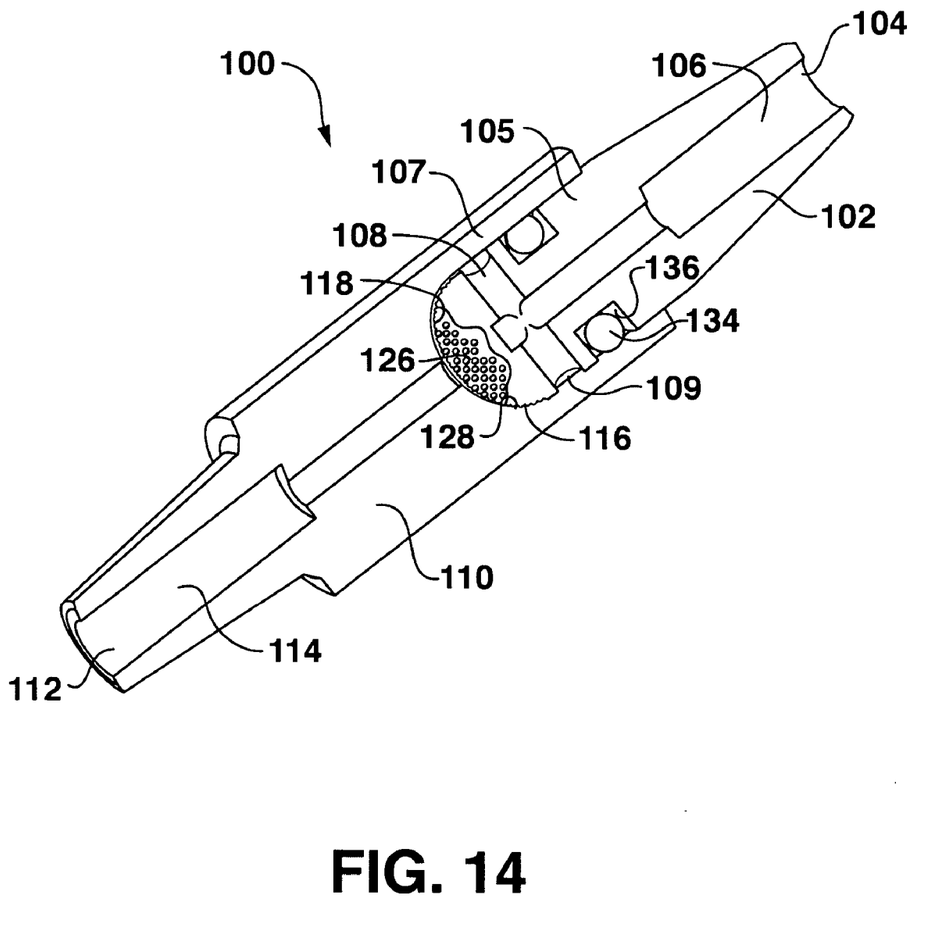
FIG. 14 is a cross-sectional view of an additional embodiment of a flow restrictor according to the invention.

The flow restrictor 100 illustrated in FIG. 14 is similar to that of FIGS. 12-13 with the exception of the shape of the opposed flow restriction surfaces 116, 118. A semispherical protrusion 126 at the forward end of the inlet housing member 102 defines the first flow restriction surface 116 having a pattern of fluid flow passages similar to that illustrated in the embodiment of FIG. 11. A correspondingly shaped semispherical recess 128 defined in the outlet housing member 110 defines the second flow restriction surface 118 having a relatively smooth surface.

Figure 15:
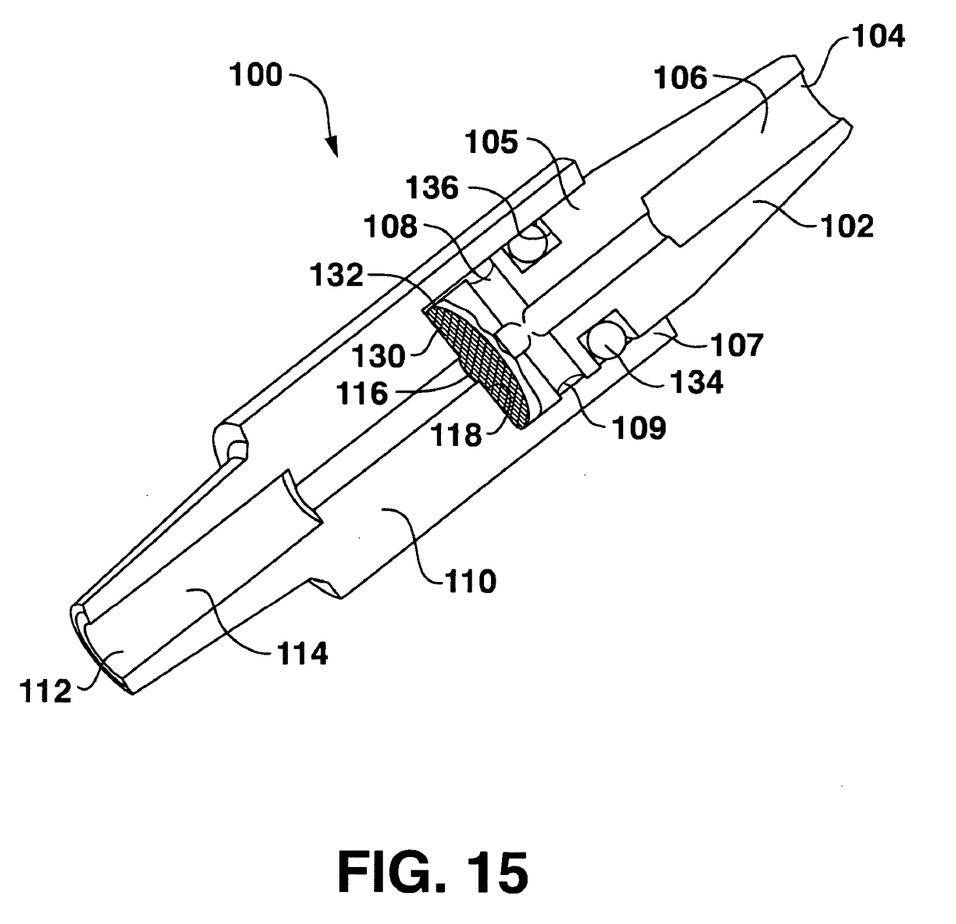
FIG. 15 is a cross-sectional view of still another embodiment of a flow restrictor according to the invention.

In the embodiment of a flow restrictor 100 shown in FIG. 15, the opposed flow restriction surfaces 116, 118 are defined as planar surfaces oriented in a plane generally perpendicular to a longitudinal axis of the restrictor 110. The first flow restriction surface 116 is defined on the planar front end 130 of the inlet housing member 102 as a grid pattern of fluid flow passages, and the opposing second flow restriction surface 118 is defined on the planar surface of the cylindrical recess 132 having a smooth surface.

It should be appreciated that any number of various shapes and configurations of components may be used to define the opposed flow restriction surfaces 116, 118.

As with the other embodiments of the flow restrictor described above, the inlet 104 and outlet 112 of the housing members may be connectable to tubing in a fluid delivery system, particularly a medical system, such that the restrictor is placeable in-line within such a system.

The predetermined compressive force used to achieve the desired flow rate may be determined in various ways. For example, the flow rate may be calculated from know variables and geometries related to the housing members 102, 110, such as opposed surface area of the flow restriction surfaces, compressibility of the housing member materials, pressure of fluid through the system, geometry of the flow passages, and so forth. This calculated compressive force may then be used to assemble the components together.

Alternatively, the compressive force may be empirically determined in a carefully controlled simulation. For example, the components may be assembled in a testing apparatus that measures compressive force and flow rate through the restrictor as the compressive force is applied. Thus, flow rate as a function of compressive force may be readily determined for housing members of a given geometry, material, etc. It is well within the level of those skilled in the arts to configure various suitable machines that may be used for determining the desired compressive force between the housing members.

It should be appreciated by those skilled in the art that modifications and variations may be made to the embodiments described above without departing from the scope and spirit of the invention. It is intended that the invention include these and other modifications as come within the scope and spirit of the appended claims and their equivalents.

What is claimed is:

1. A medical apparatus flow restrictor, comprising:
a housing having an inlet and an outlet, and a fluid flow path defined through said housing between said inlet and said outlet;
at least one pair of opposed restriction surfaces in contact with each other in an axial direction within said housing between said inlet and said outlet, a first one of said surfaces being carried on a first continuous rigid restriction device, the second one of said surfaces being carried on a second rigid restriction device that is continuous except for at least one opening therethrough, said opening being disposed in communication with said inlet and said outlet, said restriction devices defining outermost peripheral edges, said restriction surfaces disposed in said flow path such that fluid delivered to said inlet passes between said opposed restriction surfaces via said outermost peripheral edges of said restriction devices and said opening of said first continuous restriction device prior to flowing from said outlet; and
wherein at least one of said restriction surfaces comprises a pattern of fluid passages formed into said surface, said passages having a size and shape and cooperating with said opposed restriction surface such that a desired flow rate of fluid is achieved through said restrictor.

2. The flow restrictor as in claim 1, wherein said pattern of fluid flow passages is defined as a repeating geometric pattern.

3. The flow restrictor as in claim 1, wherein said pattern of fluid flow passages is defined as a continuous spiral.

4. The flow restrictor as in claim 1, wherein said pattern of fluid flow passages is defined as a plurality of spirals.

5. The flow restrictor as in claim 1, wherein said pattern of fluid flow passages is defined as a grid.

6. The flow restrictor as in claim 1, wherein said pattern of fluid flow passages is machined, etched, or cut into said restriction surface.

7. The flow restrictor as in claim 1, wherein said restriction devices comprise opposed flat planar members disposed within said housing such that fluid from said inlet flows radially between said opposing restriction surfaces of said flat planar members.

8. The flow restrictor as in claim 1, wherein said housing comprises an inlet housing member and a separate outlet housing member mated with said inlet housing member, said opposed flow restriction surfaces defined on opposed surfaces of said inlet and outlet housing members.

9. The flow restrictor as in claim 8, wherein one of said opposed flow restriction surfaces is formed in a recess of one of said housing members, and the other of said respective restriction surfaces is formed on a protrusion of the other respective said housing member that extends into said recess.

10. The flow restrictor as in claim 9, wherein said protrusion comprises a tapered conical forward portion of said inlet housing member, and said recess comprises a corresponding tapered conical configuration in said outlet housing member.

11. The flow restrictor as in claim 9, wherein said protrusion comprises a generally semi-spherical configuration, and said recess comprises a corresponding semi-spherical configuration.

12. The flow restrictor as in claim 9, wherein said protrusion comprises a generally flat planar surface, and said recess comprises a corresponding flat planar surface.

13. The flow restrictor as in claim 1, wherein said opposed flow restriction surfaces are pressed together to a predetermined degree sufficient for providing a desired fluid flow through said restrictor.

14. The flow restrictor as in claim 1, wherein a plane between said opposed flow restriction surfaces is generally perpendicular to an axis of said inlet and said outlet.

15. The flow restrictor as in claim 1, wherein a plane between said opposed flow restriction surfaces is a generally conical plane with respect to an axis of said inlet and said outlet.

16. The flow restrictor as in claim 1, wherein a plane between said opposed flow restriction surfaces is a generally curved plane with respect to an axis of said inlet and said outlet.

17. A medical fluid delivery system configured to deliver a fluid from a source to a patient at a regulated flow rate, said system comprising delivery tubing and a flow restrictor placed in-line in said tubing, said flow restrictor further comprising:
   a housing having an inlet and an outlet, and a fluid flow path defined through said housing between said inlet and said outlet;
   at least one pair of opposed restriction surfaces in contact with each other in an axial direction within said housing between said inlet and said outlet, a first one of said surfaces being carried on a first continuous rigid restriction device, the second one of said surfaces being carried on a second rigid restriction device that is continuous except for at least one opening therethrough, said opening being disposed in communication with said inlet and said outlet, said restriction devices defining outermost peripheral edges, said restriction surfaces disposed in said flow path such that fluid delivered to said inlet passes between said opposed restriction surfaces via said outermost peripheral edges of said restriction devices and said opening of said first continuous restriction device prior to flowing from said outlet; and
   wherein at least one of said restriction surfaces comprises a pattern of fluid passages formed into said surface, said passages having a size and shape and cooperating with said opposed restriction surface such that a desired flow rate of fluid is achieved through said restrictor.

18. The fluid delivery system as in claim 17, wherein said flow restrictor is disconnectable from said tubing.

19. The fluid delivery system as in claim 18, wherein said restriction devices comprise opposed flat planar members disposed within said housing such that fluid from said inlet flows radially between said opposing restriction surfaces of said flat planar members.

20. The fluid delivery system as in claim 17, wherein said pattern of fluid flow passages is defined as a repeating geometric pattern.

21. The fluid delivery system as in claim 17, wherein said pattern of fluid flow passages is defined as a spiral.

22. The fluid delivery system as in claim 17, wherein said pattern of fluid flow passages is defined as a grid.

23. The fluid delivery system as in claim 17, wherein said housing comprises an inlet housing member and a separate outlet housing member mated with said inlet housing member, said opposed flow restriction surfaces defined on opposed surfaces of said inlet and outlet housing members.

* * * * *